United States Patent
Tholey et al.

(10) Patent No.: US 10,391,671 B2
(45) Date of Patent: Aug. 27, 2019

(54) PROCESS FOR PRODUCING A NON-DENSE SINTERED CERAMIC MOLDED BODY HAVING AT LEAST TWO LAYERS

(71) Applicant: Vita Zahnfabrik H. Rauter GmbH & Co. KG, Bad Sackingen (DE)

(72) Inventors: Michael Tholey, Bad Sackingen (DE); Michael Dorn, Bad Sackingen (DE); Michael Godiker, Bad Sackingen (DE); Norbert Thiel, Bad Sackingen (DE)

(73) Assignee: Vita Zahnfabrik H. Rauter GmbH & Co. KG, Bad Säckingen (DE)

( * ) Notice: Subject to any disclaimer, the term of this patent is extended or adjusted under 35 U.S.C. 154(b) by 34 days.

(21) Appl. No.: 14/391,042

(22) PCT Filed: Apr. 16, 2013

(86) PCT No.: PCT/EP2013/057917
§ 371 (c)(1),
(2) Date: Oct. 7, 2014

(87) PCT Pub. No.: WO2013/156483
PCT Pub. Date: Oct. 24, 2013

(65) Prior Publication Data
US 2015/0246459 A1 Sep. 3, 2015

Related U.S. Application Data

(60) Provisional application No. 61/644,055, filed on May 8, 2012.

(30) Foreign Application Priority Data

Apr. 16, 2012 (EP) .................................... 12164282

(51) Int. Cl.
B28B 1/00 (2006.01)
C04B 35/48 (2006.01)
(Continued)

(52) U.S. Cl.
CPC ............ *B28B 1/008* (2013.01); *A61C 13/083* (2013.01); *A61C 13/09* (2013.01); *B32B 18/00* (2013.01);
(Continued)

(58) Field of Classification Search
CPC .. C04B 2235/3246; B28B 1/008; B28B 18/00
See application file for complete search history.

(56) References Cited

U.S. PATENT DOCUMENTS 4,316,964 A   2/1982  Lange
4,431,451 A   2/1984  Mabie et al.
(Continued)

FOREIGN PATENT DOCUMENTS

CA   1251305   3/1989
DE   102006024489 A1 * 11/2007 ......... A61C 13/0022
(Continued)

OTHER PUBLICATIONS

DE 10 2006 024489 A1 (Schlechtriemen) Nov. 29, 2007 (English language machine translation). [online] [retrieved Jul. 2, 2016]. Retrieved from: Espacenet.*

(Continued)

*Primary Examiner* — Erin Snelting
(74) *Attorney, Agent, or Firm* — Christensen, Fonder, Dardi & Herbert PLLC; Curtis B. Herbert

(57) ABSTRACT

A process for producing a non-dense sintered ceramic molded body having at least two layers, wherein a first powdery ceramic material forming a layer is contacted with at least a second powdery material forming at least a second layer; said first powdery material has a presintering temperature $T_1$ that is higher than the presintering temperature $T_s$ of said at least second powdery ceramic material; the course of a curve of shrinkage $S_1$ of said at least first powdery ceramic material differs from the course of a curve (Continued)

of shrinkage $S_2$ of said at least second powdery material, wherein curve of shrinkage $S_1$ is shifted towards higher temperatures as compared to curve of shrinkage $S_2$; and the layers are subjected to a common temperature treatment at a presintering temperature $T_s$ that is lower than the presintering temperature $T_1$ and at least equal to $T_3$ to cause sintering that remains in a stage of sintering that has not proceeded to the theoretical density; wherein the curve of shrinkage $S_1$ is modified by admixing at least one component having a curve of shrinkage $S_3$ which material is compatible with said powdery ceramic material into said first powdery ceramic material, i. e. has a grain size smaller than the first powdery ceramic material, to equalize the curves of shrinkage $S_1$ and $S_2$ in the region of the presintering temperature $T_s$.

6 Claims, 2 Drawing Sheets

(51) Int. Cl.
    *A61C 13/083* (2006.01)
    *C04B 35/486* (2006.01)
    *C04B 38/00* (2006.01)
    *A61C 13/09* (2006.01)
    *B32B 18/00* (2006.01)
    *C04B 111/00* (2006.01)

(52) U.S. Cl.
    CPC ............ *C04B 35/48* (2013.01); *C04B 35/486* (2013.01); *C04B 38/00* (2013.01); *C04B 2111/00836* (2013.01); *C04B 2235/3246* (2013.01); *C04B 2235/5409* (2013.01); *C04B 2235/5445* (2013.01); *C04B 2235/5472* (2013.01); *C04B 2235/661* (2013.01); *C04B 2235/77* (2013.01); *C04B 2235/9615* (2013.01); *C04B 2235/9661* (2013.01); *C04B 2237/066* (2013.01); *C04B 2237/068* (2013.01); *C04B 2237/341* (2013.01); *C04B 2237/348* (2013.01); *C04B 2237/403* (2013.01); *Y10T 428/24997* (2015.04)

(56) References Cited

U.S. PATENT DOCUMENTS

| | | | |
|---|---|---|---|
| 4,558,018 A * | 12/1985 | Matsuhiro | C04B 35/584 264/668 |
| 4,820,667 A | 4/1989 | Tsunekawa et al. | |
| 5,009,597 A | 4/1991 | Schaefer | |
| 5,300,324 A | 4/1994 | Croft et al. | |
| 5,578,349 A | 11/1996 | Koshkarian et al. | |
| 6,022,819 A | 2/2000 | Panzera et al. | |
| 6,576,182 B1 * | 6/2003 | Ravagni | B32B 18/00 210/490 |
| 7,056,851 B2 | 6/2006 | Nawa | |
| 7,229,286 B2 | 6/2007 | Jones et al. | |
| 7,399,722 B2 | 7/2008 | Shikata et al. | |
| 2001/0033039 A1 * | 10/2001 | Lauf | B22F 7/06 264/44 |
| 2002/0031675 A1 | 3/2002 | Cales et al. | |
| 2004/0081765 A1 | 4/2004 | Pitts et al. | |
| 2004/0108629 A1 * | 6/2004 | Imanaka | H01L 21/481 264/614 |
| 2004/0232576 A1 | 11/2004 | Brodkin et al. | |
| 2011/0177424 A1 * | 7/2011 | Goto | H01M 4/861 429/481 |
| 2012/0034446 A1 * | 2/2012 | Tohma | B01D 39/2079 428/304.4 |
| 2013/0221554 A1 * | 8/2013 | Jung | B32B 18/00 264/16 |
| 2013/0255850 A1 | 10/2013 | Thiel et al. | |

FOREIGN PATENT DOCUMENTS

| | | |
|---|---|---|
| EP | 0364281 A2 | 4/1990 |
| EP | 1510187 A2 | 3/2005 |
| EP | 1859757 A2 | 11/2007 |
| EP | 1859758 A1 | 11/2007 |
| EP | 1900341 B1 | 5/2011 |
| JP | 2002153492 | 5/2002 |
| JP | 2004035322 | 2/2004 |
| WO | 02076907 A1 | 10/2002 |
| WO | 2004009503 A1 | 1/2004 |
| WO | 2006120254 A2 | 11/2006 |
| WO | 2007028787 A1 | 3/2007 |
| WO | 2007137696 A2 | 12/2007 |
| WO | 2008106958 A2 | 9/2009 |

OTHER PUBLICATIONS

Craig, "Dental Materials", Ullmann's Encyclopedia of Industrial Chemistry, vol. 11, p. 112, Published on line: Apr. 15, 2006.
Vita Zahnfabrik, "Vitablocs Working Instructions", Date of Issue: Aug. 2012 (8 pages).
Japanese Office Action dated Apr. 4, 2017, Reference No. GNP-10473; Mailing No. 139030; 5 pages.

* cited by examiner

Lightness level

Fig. 2a LL0

| | |
|---|---|
| 100% component 1 | 1 |
| 80% component 1 : 20% component 2 | 2 |
| 60% component 1 : 40% component 2 | 3 |

| L | a | b |
|---|---|---|
| 89,49 | -0,53 | 0,71 |
| 87,33 | -2,49 | 10,48 |
| 86,09 | -2,17 | 14,01 |

Fig. 2b LL1

| |
|---|
| 80% component 1 : 20% component 2 |
| 60% component 1 : 40% component 2 |
| 40% component 1 : 60% component 2 |

| L | a | b |
|---|---|---|
| 87,33 | -2,49 | 10,48 |
| 86,09 | -2,17 | 14,01 |
| 82,33 | -0,08 | 19,26 |

Fig. 2c LL2

| |
|---|
| 60% component 1 : 40% component 2 |
| 40% component 1 : 60% component 2 |
| 20% component 1 : 80% component 2 |

| L | a | b |
|---|---|---|
| 86,09 | -2,17 | 14,01 |
| 82,33 | -0,08 | 19,26 |
| 79,45 | 1,76 | 20,81 |

Fig. 2d LL3

| |
|---|
| 40% component 1 : 60% component 2 |
| 20% component 1 : 80% component 2 |
| 100% component 2 |

| L | a | b |
|---|---|---|
| 82,33 | -0,08 | 19,26 |
| 79,45 | 1,76 | 20,81 |
| 76,27 | 3,59 | 23,11 |

Fig. 2

PROCESS FOR PRODUCING A NON-DENSE SINTERED CERAMIC MOLDED BODY HAVING AT LEAST TWO LAYERS

CROSS REFERENCE TO RELATED APPLICATIONS

This application is a national stage filing of PCT Application No. PCT/EP2013/057917, which claims priority to European Patent Application No. 12164282.1 filed Apr. 16, 2012 and to U.S. Provisional Application No. 61/644,055 filed May 8, 2012, each of which are incorporated herein by reference.

TECHNICAL FIELD

The present invention relates to a process for producing a non-dense sintered ceramic molded body having at least two layers and to a molded body obtainable by the process according to the invention.

INTRODUCTION AND SUMMARY OF THE INVENTION

The use of glass-ceramic restorations has proven effective for the restoration of dental defects, especially in the region of the mouth. Because of the low strength of such restorations as compared to those made of stabilized zirconia, these materials, which meet aesthetic requirements, are not indicated for the preparation of bridges or for restoring patients suffering from masticatory disorders (bruxism). For the preparation of posterior bridges or crowns, it has been usual to produce scaffolds of a high strength material, which subsequently need to be faced with a glass ceramic layer. If fully anatomical crowns or minimally reduced crowns are to be produced by CAD/CAM technologies, the blanks obtained are only glazed or provided with a thin veneer layer. This is an alternative to a cast crown and is not to be recognized as a restoration if possible. However, this requires that the crown is not unicolored, but has a multicolored design, a color gradient running from the tooth neck towards the incisal edge/occlusal surface from dark to light in order to reproduce the color gradient of a natural tooth as exactly as possible.

Articles made of zirconia, especially for dental purposes, have become established because of their comparatively high bending strength. However, the common zirconia materials for dental purposes are unicolored and can be immediately recognized as a restoration because of their light color. Therefore, copings for crowning prepared therefrom must always be faced in order that the restoration fits aesthetically into the remaining teeth. In order to achieve a natural coloring, porous monolithic zirconia restorations, which may also have been precolored in a single color, are matched with coloring liquids to the individual situation in the patient.

EP 1 859 757 A discloses $ZrO_2$-based compositions as well as unicolored and multicolored blanks made of oxide ceramics, and a process for the preparation thereof, in which a) oxide-ceramic powders are coated with a coloring substance, b) the coated powders are preferably classified, and at least one colored powder is filled into a compression mold, c) the colored powder or powders is/are compressed into a molded body, and d) the compressed molded body is sintered into a blank, and the use of such blanks for preparing dental restorations.

EP 1 859 758 A discloses a block body of ceramic compositions, especially feld-spar-based dental compositions, consisting of at least one ceramic composition with predefined first optical properties and at least one second ceramic composition with predefined second optical properties, and a transition zone between the two ceramic compositions constituted of varying blends of said at least two ceramic compositions, the variation gradient of the blends being essentially constant.

EP 1 900 341 A discloses a multicolored molded body, especially made of feldspar ceramics, with superimposed layers for preparing dental prostheses, at least two successive layers of different colors and at least two intermediate layers of different colors between at least two successive primary layers of different colors, wherein between these intermediate layers a change of the color takes place along a direction that is opposite to the direction of the change in color between the primary layers.

WO 2007/137696A discloses green body consisting of at least two different molding powder mixtures each containing a ceramic powder, and a coloring metal compound and/or a coloring pigment which are compressed to form the green body. The green body ceramics are particularly suitable as color-graded dental ceramics (blanks), which serve as all-ceramic restorations. The powder mixtures can consist out of a zirconia granulate and a zirconium silicate material, in which the zirconium silicate changes the chemical structure and lowers the mechanical properties (e.g. 3-point bending strength).

Iron oxides, for example, are used for coloring zirconia granules. These or similar additives influence the sintering behavior because they change the sintering activity. Thus, a more intensely colored region can differ from a less intensely colored region in terms of shrinkage or density at the same temperature. This deviating sintering behavior unavoidably provokes deformation of the original geometry, if the sintering process is stopped before the theoretical density is reached, in favor of improved processability.

Mixing pigmented and non-pigmented zirconia granules basically enables the preparation of a color-layered geometry or the production of a three-dimensional gradient. For processing by CAD/CAM technology, it is necessary that such blocks or disks are presintered at a particular temperature in order to ensure good grindability. The presintering essentially corresponds to an intermediate stage on the way to the final dense sintering, as close as possible to the theoretical density. However, the presintering of multicolored blocks is problematic because a sintering distortion between lighter and darker regions occurs in the mentioned intermediate stage. This distortion is caused by different sintering activities, which are primarily due to the proportion of coloring components. However, since the final sintering density of the layers as achieved in dense sintering is almost identical, the ground object would again become distorted from the intermediate stage to the final stage.

To date, no solutions have been known that enable the production of a color gradient in zirconia blanks in such a way that they can be subsequently processed in a porous sintered state.

Indeed, it would be basically possible to circumvent the difficulties by determining the sintering distortion in advance and calculating a correction during the processing by CAM software. However, this method would reach the limits of travel paths of the CAM machines when there are undercuts, and therefore is not workable in practice. Also, this method does not achieve the object of the invention.

It is desirable to adjust colored and colorless powders or granules of zirconia in such a way that they do not exhibit distortion in the processable intermediate stage and in the final density, i.e., after processing and dense sintering.

The object of the invention is achieved by a process for producing a non-dense sintered ceramic molded body having at least two layers,
wherein a first powdery ceramic material forming a layer is contacted with at least a second powdery material forming at least a second layer;
said first powdery material has a presintering temperature $T_1$ that is higher than the presintering temperature $T_S$ of said at least second powdery ceramic material;
the course of a curve of shrinkage $S_1$ of said at least first powdery ceramic material differs from the course of a curve of shrinkage $S_2$ of said at least second powdery material, wherein curve of shrinkage $S_1$ is shifted towards higher temperatures as compared to curve of shrinkage $S_2$; and
the layers are subjected to a common temperature treatment at a presintering temperature $T_S$ that is lower than the presintering temperature $T_1$ and at least equal to $T_3$ to cause sintering that remains in a stage of sintering that has not proceeded to the theoretical density; wherein
the curve of shrinkage $S_1$ is modified by admixing at least one component having a curve of shrinkage $S_3$ which material is compatible with said powdery ceramic material into said first powdery ceramic material, i. e. has a grain size smaller than the first powdery ceramic material, to equalize the curves of shrinkage $S_1$ and $S_2$ in the region of the presintering temperature $T_S$.

The compatibility of the compensation powder depends on the grain size of used components. By mixing and pressing these different powders no pores or inhomogeneities should derange the sintered or presintered structure.

An advantage of the process according to the invention resides in the fact, among others, that the relevant properties of a known material are maintained while the optical properties can be controlled in a desired direction. Thus, for example, it is possible to design the block with differently colored layers in almost any number. Further, it is also possible to produce a multicolored block by continuous mixing methods and by using just a few starting colors, wherein the color grading may also be a continuous gradient.

The process according to the invention enables the coloring of yttrium-stabilized zirconium layers, which can be arranged as superimposed blocks. Thus, the user gets the possibility to use for restorations made of zirconia respectively the same starting material that has already been largely used for unicolored dental prostheses or dental replacement scaffolds. The physical properties remain essentially unchanged as compared to the established product. Disturbing or time-consuming operations, such as the coloring of the scaffolds or the facing of the scaffolds, can be reduced to a minimum or are superfluous. Color variations in the restoration to be produced can be defined by a simulation with the software designated for the processing. After the CAD/CAM production off the restoration, the sintering process performed to dense sintering, a glaze layer can be applied if desired.

In one embodiment of the process according to the invention, the first powdery ceramic material contains yttrium-stabilized zirconia, which is commercially available, for example, as granules from the company TOSOH, Japan, under the designation TZ-3YSB-C (Curve $S_1$, $T_1$).

In a further embodiment of the process according to the invention, the at least second powdery ceramic material contains yttrium-stabilized zirconia that exhibits a more intense coloring than that of the first powdery ceramic material. The at least second powdery ceramic material is commercially available, for example, as granules from the company TOSOH, Japan, under the designation TZ-Yellow-SB-C. (Curve $S_2$, $T_S$).

In another embodiment of the process according to the invention, the component admixed into the first powdery ceramic material is, for example, the granules obtainable from the company TOSOH, Japan, under the designation TZ-PX-242A or Zpex (Curve $S_3$, $T_3$).

In particular, the presintering temperature $T_1$ according to the present invention is within a range of from 900° C. to 1300° C., especially from 950° C. to 1150° C., from 1000° C. to 1100° C., or from 1040° C. to 1080° C., $T_S$ is within a range of from 850° C. to 1250° C., and/or $T_3$ is within a range of from 800° C. to 1200° C.

BRIEF DESCRIPTION OF THE DRAWINGS

FIG. 2 schematically shows a three-layer block according to the present invention.

DETAILED DESCRIPTION

Figure 1:
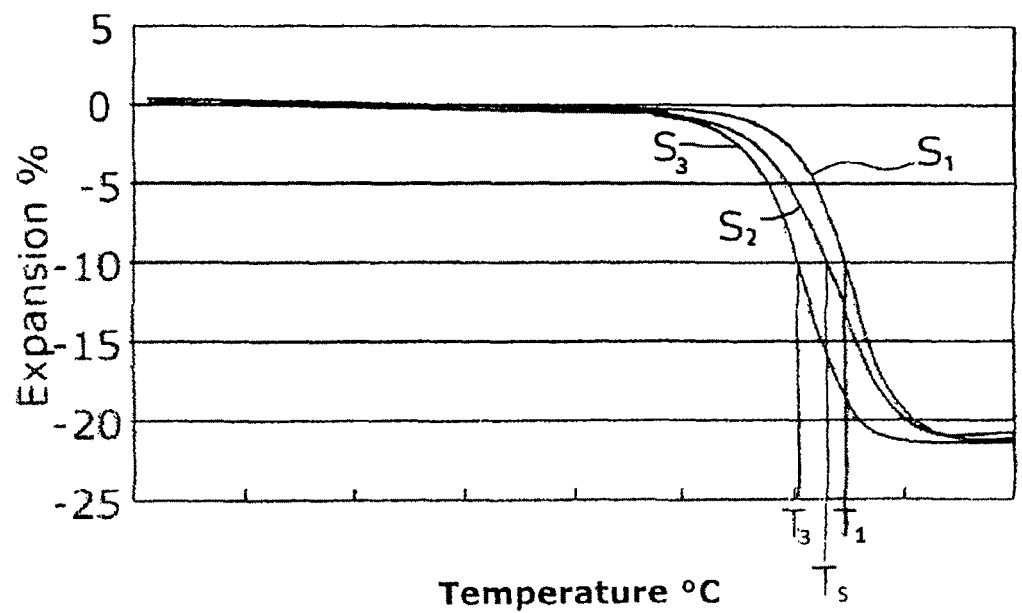
FIG. 1 shows schematically the shrinking behavior for 3 different materials during sintering (in a representation of three curves of shrinkage).

The invention is explained in more detail in the following. FIG. 1 schematically shows the course of the curves $S_1$, $S_2$ during sintering of the first and second powdery ceramic materials. The presintering temperatures of the first and second powdery ceramic materials are designated as $T_1$ and $T_S$. "Presintering temperature" means the temperature that is lower than the corresponding sintering temperature of the respective material at which dense sintering to the theoretical density or at least to very close to the theoretical density occurs. The curve of shrinkage of the component compatible with the first powdery ceramic material is designated as $S_1$ in FIG. 1. $T_S$ is the presintering temperature at which the layers forming the molded body are subjected to the common temperature treatment to form a porous sintered molded body.

For example, the first powdery ceramic material is white or only weakly colored, and the second powdery ceramic material represents a more intensely couloured powdery ceramic material having a grain size in the range of the first powdery ceramic material. The third curve $S_3$ has a smaller grain size than the first powdery ceramic material. The curves of shrinkage $S_1$ and $S_2$ of the two powdery ceramic ground materials are so much different that the disadvantageous distortions of the first and second layers occur.

Surprisingly, admixing a component with a curve of shrinkage $S_3$ compatible with the first powdery ceramic material to the first powdery ceramic material can equalize its curve of shrinkage $S_1$ to the curve of shrinkage $S_2$ of the second powdery ceramic material within the range of the selected presintering temperature, or even achieve identical curves of shrinkage. The shifting of the curve of shrinkage $S_1$ depends on the level of admixing the component compatible with the first powdery ceramic material. The compatibility of the component with curve $S_3$ is related with its smaller grain size compared with the first powdery ceramic material. In particular the difference in grain size of the two materials is at least 5%, more particularly 10% or 20% or even 30% or more such as 40%.

Said component compatible with the first powdery ceramic material may be, for example, a zirconia material containing, in addition to yttria in the percent range, especially 6-7%: less than one percent of alumina, traces of silica, and iron oxide as a pigment, wherein less alumina is present as compared to the first powdery ceramic material. The particle size of the component is smaller than that of the first powdery ceramic material, and typically the size of the particles of the component is about half the size of the particles of the first powdery ceramic material, whose particle size is within a range of 80-100 nm. The BET value of the component to be admixed is about double the BET value of the first powdery ceramic material. Typical BET values for the component to be admixed are 11-15 m²/g. Such materials are commercially available and are distributed under the designation TZ-PX-242A or Zpex from TOSOH, Japan, for the component to be admixed, and under the designation TZ-3YSB-C, TOSOH, Japan, for the first powdery ceramic material. The material forming component 2 is the at least second powdery ceramic material according to the present invention, being provided with a higher pigmentation, typically in the form of iron oxide, as compared to the first powdery ceramic material. Iron oxide has a yellowish color.

The following table shows properties of a special first and second powdery ceramic material.

|  | TZ-PX-242A | TZ-3YSB-C |
| --- | --- | --- |
| Crystallite Size [nm] | 32 | 36 |
| Particle size D50 [µm] | 0.43 | 0.60 |
| Granule Size [µm] | 52 | 60 |
| Bulk Density [g/cm³] | 1.06 | 1.20 |
| Specific surface area [m²/g] | ca. 12 | ca. 6 |

The component compatible with the first powdery ceramic material is admixed with the first powdery ceramic material in proportions within a range of 25 percent by weight to 50 percent by weight (especially from 30 to 40% by weight) in order to achieve the effect of equalizing the curves of shrinkage as desired according to the invention.

The molded bodies according to the invention, which can be prepared by applying the process according to the invention, advantageously show no distortions that are due to sintering distortion after completion of the presintering, so that the molded body in this porous sintered state can be processed by material removal, and does not experience any deformation after dense sintering.

In a three-layer stacking in FIGS. 2a-d, the molded body according to the invention is schematically represented together with information about the layer composition and the color values of the individual layers according to the CIE-Lab color system. Component 1 according to FIG. 2a is a powdery ceramic material forming the first layer 1 and being a mixture consisting of white granules, for example TZ-3YSB-C and TZ-PX-242A, commercially available from TOSOH, Japan. The middle layer 2 is formed from a mixture of component 1 and a component 2. Component 2 is more intensely yellow/brown pigmented granules, for example, TZ-Yellow-SBC. In the embodiment according to FIG. 2a, layer 2 consists of a mixture of 80% component 1 and 20% component 2. The middle layer 3 is formed from a mixture of components 1 and 2 in a proportion of 60%/40%. The further embodiments shown in FIGS. 2b-d are each characterized by a more intense pigmentation.

The molded body according to the invention is advantageously prepared by intimately mixing the first powdery ceramic material with the component compatible with this material. The mixed material is filled into a mold, the forming layer is smoothed and then covered with a second layer of a mixture of component 1 and component 2. This step is repeated to form the third layer. The material is compacted under pressure (typically 100 to 200 MPa) and then released from the mold.

This is followed by a sintering process in which the temperature is raised. The temperature raise is stopped at a temperature selected in such a way that the molded body obtained can be readily machined, and subjected to dense sintering after processing. The presintering temperature is within a range of from 800° C. to 1200° C., especially from 950° C. to 1150° C., 1000-1100° C., or 1040-1080° C.

For facilitating the machining, the molded body according to the invention is provided with relevant elements known to the skilled person that are suitable for fixing the block within a CAD/CAM machine.

In a further embodiment of the process according to the invention, the porous sintered molded body obtained is further processed by forming processes.

The present invention also relates to a molded body obtainable by the process according to the invention. Advantageously, the layers are dimensionally stable in the porous sintering.

Example 1

Component 1 is obtained by intimately mixing 650 g of TZ-3YSB-C from TOSOH, Japan ($T_1$~1076° C.), with 350 g of TZ-PX-242A from TOSOH, Japan ($T_3$~1038° C.), in a mixer from the company Bachofen, type DynaMix® CM200 (or CM100, CM500, CM1000). For forming by means of an axial compression method, component 1 is filled into the stamper by means of a filling unit known to the skilled person. The layer is uniformly spread in the mold by pulling away the filling unit. Typically, the layer thickness is higher than the desired layer thickness of the final product because of the bulk density being lower than the compressed density, and depends on the raw materials employed. Typically, the filled-in layer thickness of the powder is 2.318 times the corresponding layer thickness of the compressed component and is 14.88 mm. Onto this layer, 22.29 g of a mixture of 80% by weight component 1 and 20% by weight component 2, which consists of TZ-Yellow-SBC from TOSOH, Japan, is applied. After the second layer has been filled in, it is also smoothed and thereafter covered by the third layer consisting of the intimately mixed components 1 and 2 in a mixing ratio of 60% by weight to 40% by weight. Optionally, smoothing is again performed. Thereafter, the layered structure in the mold is compacted under a pressure of 200-165 MPa to a density of 3.13 g/cm³.

After the compressed molded body has been released, it is subjected to sintering until a temperature ($T_S$) of 1060° C. is reached. The molded body can be processed into multi-unit bridges by means of CAD/CAM methods. The bridges obtained are dense sintered at temperatures of 1530° C.

The corresponding colors of the individual layers can be seen from FIG. 2a.

The sintered block is provided with a holding member. This is realized by adhesive-bonding the block and holding member. The porous ceramic component is placed by means of a centering device onto the holding member fixed in a base plate and provided with adhesive, and is thus fixed.

Example 2

The blocks shown in FIGS. 2b to 2d were prepared by analogy with Example 1, the following mixing ratios of components 1 and 2 being employed:

| Block according to | Layer 1 Comp. 1 to comp. 2 [% by weight] | Layer 2 Comp. 1 to comp. 2 [% by weight] | Layer 3 Comp. 1 to comp. 2 [% by weight] |
|---|---|---|---|
| FIG. 2b | 80 to 20 | 60 to 40 | 40 to 60 |
| FIG. 2c | 60 to 40 | 40 to 60 | 20 to 80 |
| FIG. 2d | 40 to 60 | 20 to 80 | 0 to 100 |

The following Table illustrates the quantitative ranges in which the component compatible with the first powdery ceramic material can be mixed with the first powdery ceramic material in order to achieve the desired presintering temperature in the production process and to arrive at molded bodies that are according to the invention.

| Example | Proportion of TZ-3YSB-C in layer 1 [% by weight] | Proportion of TZ-PX-242A in layer 1 [% by weight] | Proportion of TZ-Yellow-SB-C in layer [% by weight] | Presintering temperature [° C.] |
|---|---|---|---|---|
| 1 | 70 | 30 | 100 | 1066 |
| 2 | 60 | 40 | 100 | 1066 |
| 3 | 50 | 50 | 100 | 1066 |

What is claimed is:

1. A process for producing a non-dense sintered ceramic molded body for dental purposes having at least two layers comprising
    contacting and pressing, in a mold for a blank for forming a dental restoration, at least a first powdery ceramic material forming a first layer with at least a second powdery ceramic material forming at least a second layer, thereby producing a molded body;
    wherein said at least first powdery ceramic material has a presintering temperature $T_1$ that is higher than a presintering temperature $T_S$ of said at least second powdery ceramic material;
    the course of a curve of shrinkage $S_1$ of said at least first powdery ceramic material differs from the course of a curve of shrinkage $S_2$ of said at least second powdery material, wherein curve of shrinkage $S_1$ is shifted towards higher temperatures as compared to curve of shrinkage $S_2$; and
    presintering the molded body by subjecting the layers to a common temperature treatment at the presintering temperature $T_S$ which is in a range from 850° C. to 1250° C. and that is lower than the presintering temperature $T_1$ which is in a range of from 900° C. to 1300° C. and that is at least equal to presintering temperature $T_3$ which is within a range of from 850° C. to 1200° C., to cause sintering that remains in a stage of sintering that has not proceeded to the theoretical density, with the molded body showing no distortions that are due to sintering distortion after completion of presintering the molded body;
    wherein the at least first powdery ceramic material having the curve of shrinkage $S_1$ is admixed with at least one component material that has the presintering temperature $T_3$ and has a curve of shrinkage $S_3$ which component material has a grain size smaller than the at least first powdery ceramic material, with the admixed materials having a curve of shrinkage that is between the curves of shrinkage $S_1$ and $S_3$ in the presintering temperature $T_S$ range from 850° C. to 1250° C.,
    and wherein the at least second powdery ceramic material contains yttrium stabilized zirconia that exhibits a more intense coloring than the first powdery ceramic material; and
    wherein the at least one component material is admixed with the at least first powdery ceramic material in proportions within a range of 25 to 50 wt %.

2. The process according to claim 1, wherein said at least first powdery ceramic material contains yttrium-stabilized zirconia.

3. The process according to claim 1, wherein the non-dense sintered molded body obtained is further processed by forming processes.

4. The process of claim 1 further comprising obtaining the blank from the mold and machining the blank to provide a dental prosthesis, a dental replacement scaffold, a bridge, or a crown.

5. The process of claim 1 further comprising removal of material from the presintered molded body and then performing dense sintering on the presintered molded body wherein the dense sintering does not cause deformation of the presintered molded body.

6. A process for producing a non-dense sintered ceramic molded body for dental purposes having at least two layers, comprising
    contacting and pressing, in a mold for a blank for forming a dental restoration, at least a first powdery ceramic material forming a first layer with at least a second powdery ceramic material forming at least a second layer, thereby producing a molded body;
    wherein said at least first powdery ceramic material has a presintering temperature $T_1$ that is higher than a presintering temperature $T_S$ of said at least second powdery ceramic material;
    the course of a curve of shrinkage $S_1$ of said at least first powdery ceramic material differs from the course of a curve of shrinkage $S_2$ of said at least second powdery material, wherein curve of shrinkage $S_1$ is shifted towards higher temperatures as compared to curve of shrinkage $S_2$; and
    presintering the molded body by subjecting the layers to a common temperature treatment at the presintering temperature $T_S$ which is in a range from 850° C. to 1250° C. and that is lower than the presintering temperature $T_1$ which is in a range of from 900° C. to 1300° C. and that is at least equal to presintering temperature $T_3$ which is within a range of from 850° C. to 1200° C., to cause sintering that remains in a stage of sintering that has not proceeded to the theoretical density, with the molded body showing no distortions that are due to sintering distortion after completion of presintering the molded body;
    wherein the at least first powdery ceramic material having the curve of shrinkage $S_1$ is admixed with at least one component material that has the presintering temperature $T_3$ and has a curve of shrinkage $S_3$ which component material has a grain size smaller than the at least first powdery ceramic material, with the admixed materials having a curve of shrinkage that is between the curves of shrinkage $S_1$ and $S_3$ in the presintering temperature $T_S$ range from 850° C. to 1250° C.;

and wherein the at least first powdery ceramic material, the at least second powdery ceramic material, the at least one component material, the first layer, and the second layer each consist essentially of a ceramic;

and wherein the at least second powdery ceramic material contains yttrium-stabilized zirconia that exhibits a more intense coloring than the at least first powdery ceramic material.

* * * * *